United States Patent [19]
Friedman

[11] Patent Number: 5,421,350
[45] Date of Patent: Jun. 6, 1995

[54] CONDOM HAVING ADHESIVE MEANS

[76] Inventor: Leah Friedman, 5405 12th Ave., Apartment 1, Brooklyn, N.Y. 11219

[21] Appl. No.: 206,935

[22] Filed: Mar. 7, 1994

[51] Int. Cl.⁶ .................................................. A61F 6/04
[52] U.S. Cl. ..................................... 128/844; 128/918; 128/842
[58] Field of Search ....................... 128/842, 844, 918; 604/347–353

[56] References Cited

U.S. PATENT DOCUMENTS

| | | | |
|---|---|---|---|
| 2,703,574 | 3/1955 | Hirschfeld | 128/844 |
| 3,037,508 | 6/1962 | Friedman | 128/844 |
| 3,648,700 | 3/1972 | Warner | 128/844 |
| 4,320,752 | 3/1982 | Comparetto | 128/844 |
| 4,821,742 | 4/1989 | Phelps | 128/844 |
| 4,869,269 | 9/1989 | Sharkan | 128/844 |
| 4,955,392 | 9/1990 | Sorkin | 128/844 |

Primary Examiner—Michael A. Brown

[57] ABSTRACT

An improved condom is provided, which includes an unrolled condom encompassing the solely the head of a penis having a reservoir to collect semen, adhesive means to securely fasten said condom to the head of said penis, an angled condom opening to solely encompass only the head of the penis, and an internal retaining means within the center of the flange which then becomes integrately secured under the lip on the head of a penis allowing the rest of the penis shaft to be exposed, thus, increasing sensitivity during intercourse. The retaining means is anglurly designed in a functional relationship to encompass the angle of the lip of the head of the penis and the angle of the penis shaft, thus, forming a more secure fastening arrangement between penis and condom. The adhesive means is positioned throughout the top and bottom portion of the condom to securely fasten said condom to the head of a penis.

17 Claims, 1 Drawing Sheet

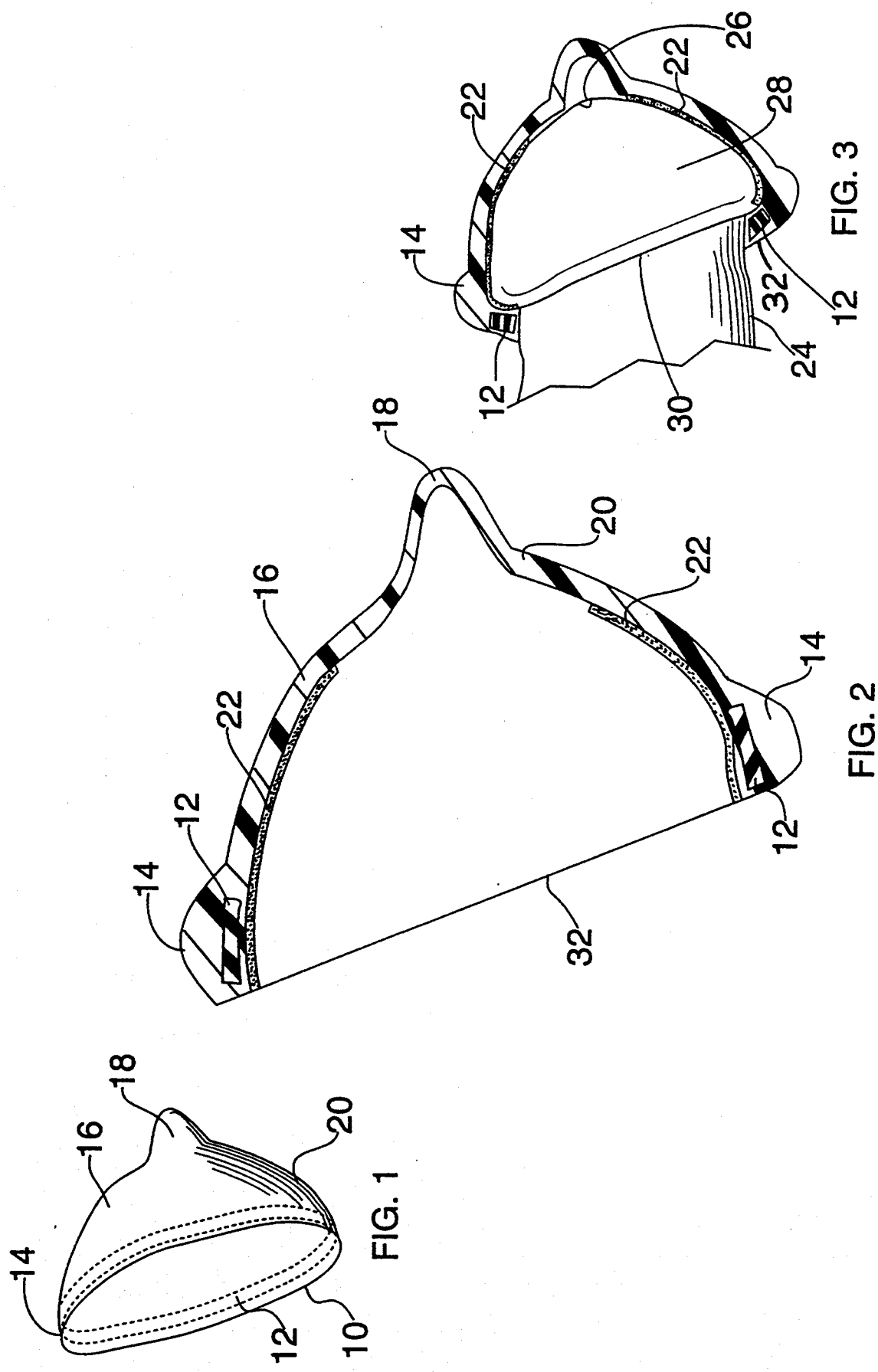

CONDOM HAVING ADHESIVE MEANS

BACKGROUND OF THE INVENTION

1. Field of the Invention

The present invention relates to condoms and more particularly to a condom an method for providing a natural feeling for the male partner during intercourse while using a condom.

More particularly, the present invention relates to the field of condom retaining apparatus.

2. Description of the Prior Art

Many people use condoms during sexual intercourse. One problem of using condoms encountered by some people is that sometimes a condom does not remain in its fully unrolled condition on the penis of a man while it is in use, and subsequently becomes loose. This situation often jeopardizes the purpose of using the condom. Therefore it is desirable to have a retaining apparatus to keep the condom in its fully unrolled condition while in use.

Therefore there is an existing need to have a condom retaining apparatus which securely keeps the condom in its unrolled position while being used, yet is not comfortable for the user. This need is particularly urgent in today's society, where a rapidly growing number of people are using the condoms for various purposes, including preventing pregnancy and the transmittal of sexually communicable diseases, such as AIDS.

While few women notice enough difference when a condom is used to avoid using one, men often avoid using condoms because they interfere with the pleasure associated with intercourse. Men complain that there is little feeling and consequently sometimes avoid using a condom even when failing to do so could have undesirable consequences or is dangerous. To overcome this problem condoms have been proposed which are either thinner or smaller in size in an attempt to help reduce the amount of interference with the natural feeling men are used to during intercourse without the use of a condom, but the objections persist.

Numerous condom devices have been provided in prior art. While these condom devices may be suitable for the particular purpose to which they address, they differ from the present invention as discussed below.

In connection with a male condom device of the type using a penis receptacle worn on the penis, it is common to use a sheath of flexible material placed over the penis.

The following prior art patents have been found to be relevant to the field of the present invention:

1. U.S. Pat. No. 3,999,550 issued to Martin on Dec. 28, 1976 for "External Male Catheter" (hereafter the "Martin Patent").

2. U.S. Pat. No. 2,379,346 issued to Farrell on Jun. 26, 1945 for "Urinal Appliance" (hereafter the "Farrell Patent").

3. U.S. Pat. No. 2,222,825 issued to Starck on Nov. 26, 1940 for "Urinal Pouch" (hereafter the "Starck Patent").

4. U.S. Pat. No. 1,982,520 issued to Jakala on Nov. 27, 1934 for "Sanitary Device" (hereafter the "Jakala Patent").

5. U.S. Pat. No. 731,201 issued to Miller et al. on Jun. 16, 1903 for "Supporting Bandage" (hereafter the "Miller Patent").

6. French Patent No. 1,508,356 issued to Rasummy on Nov. 27, 1967 for "Apparatus For Unitary Incontinence In Men" (hereafter the "Rasummy Patent").

7. French Patent No. 992,462 issued to Gamard et al. on Oct. 18, 1951 for "Apparatus For The Treatment Of Unitary Incontinence" (hereafter the "Gamard Patent").

8. German Patent No. 454,773 issued to Kohler on Jan. 17, 1928 for "Apparatus For Treatment of Male Infectious Diseases" (hereafter the "Kohler Patent").

The Miller Patent discloses a supporting bandage for retaining a medicated or absorbent compress on the head of the penis of a man. The supporting bandage comprises a waist belt to be wrapped around the man's waist, and a pair of flexible elastic strings linking the compress to the waist belt. The Miller Patent supporting bandage is not suitable for the purpose of retaining a condom in its fully unrolled condition, because it merely holds the compress on the head of the penis in a relatively motionless situation. If the same supporting bandage is used for a condom, then the flexibility and elasticity of the pair of strings will allow the condom to get loose as a result of the body movements during sexual intercourse.

The Kohler Patent discloses an apparatus for treatment of male infectious diseases. The apparatus comprises a generally oval-shaped rigid container attached to belt support by an attachment assembly. The attachment assembly includes a cap member, a disc member and a ring member which is threaded on the neck of the container. The Kohler Patent attachment is designed for mounting a rigid container, which makes it unfit for retaining a flexible condom.

The Jakala Patent discloses a sanitary device which again comprises an oval-shaped rigid container made of metal material. The rigid container is attached to the penis of a man by a wiring member. The spring tension of the wiring member holds it inside the cavity of the rigid container. It is clear that this arrangement is also not suitable for a condom.

The Stack patent discloses a large sized urinal pouch for covering the entire lower body area of a patient with bladder disability. The urinal pouch is retained under the lower body portion between the two legs of the patient by a number of strap and buckle assemblies.

The Farrell Patent discloses a urinary appliance for people having urinary problems. It comprises a rubber tube attached to the penis of a man by an attachment assembly. The attachment assembly includes a rigid or semi-rigid tubular member having a circular flange. There are two pairs of studs on the circular flange for connection with a pair of short straps and a pair of long straps, which straps are all further attached to a waist belt.

The Gamard Patent discloses an apparatus for treatment of urinary incontinence. The apparatus comprises a container having an enlarged flange attached to a waist belt through straps. The apparatus also includes an electronic treatment device which has two terminals connected into the container.

The Rasummy Patent discloses an apparatus for urinary incontinence n men, where a tubular container is retained to the penis by a band which is wrapped around the end of the tubular container and fastened by VELCRO members. A pair of short straps then connect the fastened band to a waist belt.

The Martin Patent discloses an external male catheter which is retained on the use's penis by a belt assembly.

A belt receptacle and a belt retaining ring are used for connecting the catheter and the belt assembly.

It can be seen that none of the prior art apparatus is suitable for the purpose of retaining a condom on a man's penis while it is in use. Some of the prior art patents are designed with a rigid container, such as the Kohler Patent and the Jakala Patent, which is certainly not suitable for the highly elastic and flexible condom. Some the prior art patents are designed with rigid or protruding attachment members, such as the buckles of the Starck Patent, the flange and studs of the Farrell patent and the belt receptacle and belt retaining ring of the Martin Patent, which are also not suitable for retaining a condom because the rigid or extended members will make the user for the condom uncomfortable. Other prior art patents, such as the Miller Patent, the Gamard Patent and the Rasummy Patent, use short flexible straps to connect the containers to the waist belts. As discussed before, the disadvantage of this type of arrangement is that even though the waist belt is tightly fastened to a use's waist, the short connecting straps themselves are dangling but not fastened to the user's body. They will not withstand the movements during sexual intercourse, since their flexibility and elasticity will make them act just like a swing to permit a condom to get loose.

In U.S. Pat. No. 3,863,638, Rogers shows a liner pad between the sheath and the penis to form a cushion and absorb some of the pressure exerted by an externally wound tape. Often, however, the pad is inadvertently not used by an attendant applying the device to a patient or the pad is simply too wide or too narrow for a particular penis. Additionally, Rogers indicates the use of adhesive on both sides of the pad, thus eliminating the need for an external tape.

In U.S. Pat. No. 4,187,851, Hauser also eliminates an external tape by showing the use of an adhesive on both the inner and outer surfaces of a pad. In this way, the pad can be wound around a penis, and the sheath of the urinal device rolled over the pad and held in place by the adhesive. Although the devices of Rogers and Hauser eliminate externally wound tape, they continue to present the problems which result when a material is too tightly wound about a penis.

Broerman, in U.S. Pat. No. 3,739,783, shows a urinal device to be used without wound tape or pads. An adhesive is painted onto a penis and a sheath impregnated with silicone rubber placed over the adhesive. The method and device, however, are not satisfactory since reliability continues to depend on an attendant's use of a proper adhesive.

Hence, there continues to be a need for a safe, leak-free male condom device.

CONDOM HAVING ENHANCED GRIPPABILITY STRUCTURE AND ANNULAR SEALING ELEMENT

Inventor: Robert G. Wheeler

U.S. Pat. No. 5,199,444

Condoms are disclosed of the type comprising a main sheath portion closed at the distal end and open at a proximal end thereof, which are amenable to construction form thermoplastic elastomeric materials. In one preferred aspect, such condoms comprise an annular-shaped sealing element, formed of an elastic material, circumscribing an interior opening of smaller size than the proximal end opening of the condom and joined at the outer periphery of the sealing element to the main sheath, at or in the vicinity of the proximal end opening. Such construction thereby provides a membrane dam in the proximal segment of the condom to enhance its effectiveness as a contraceptive and to minimize the incidence of sexually transmitted diseases. Also disclosed are various condom manufacturing and processing apparatuses, as well as applicators for applying the condoms to the penis of the wearer.

CONDOM RETAINING APPARATUS

Inventor: Merlyn Starley

U.S. Pat. No. 5,158,556

The present invention is a condom retaining apparatus. It comprises a pair of double-sided flexible thin bands each having a first end and a second end, and small U-shaped clipping member for attaching the first ends of the pair of double-sided flexible thin bands to the condom ring of a condom at two opposite locations. Each double-sided flexible thin band has adhesive at one side of attaching it to a user's skin on the upper thigh areas. The condom retaining apparatus is designed to keep the condom in its unrolled position while it is being used, without tearing the condom and without being uncomfortable to the user.

CONDUCTIVE CONDOM

Inventor: Gary D. Johnson

U.S. Pat. No. 5,076,287

An electrically conductive condom includes a generally cylindrical protective sheath having an open end for receiving a penis therein and an opposite closed end, the sheath being made from a thin, elastic, electrically conductive material which may be formed from a non-conductive elastic material having electrically conductive particles embedded therein. The electrically conductive material is preferably a thin elastomeric material with small conductive particles, such as carbon and/or silver particles, embedded therein. A reinforcing layer for retaining the sheath on a person, and quick release is provided for releasably securing the retaining strap about a person so as to releasably secure the sheath on the person.

CONDUCTIVE CONDOM

Inventor: Gary D. Johnson

U.S. Pat. No. 5,076,287

An electrically conductive condom includes a generally cylindrical protective sheath having an open end for receiving a penis therein and an opposite closed end, the sheath being made from a thin, elastic, electrically conductive material which may be formed from a non-conductive elastic material having electrically conductive particles embedded therein. The electrically conductive material is preferably a thin elastomeric material with small conductive particles, such as carbon and/or silver particles, embedded therein. A reinforcing layer for retaining the sheath on a person, and quick release is provided for releasably securing the retaining strap about a person so as to releasably secure the sheath on the person.

NATURAL FEELING CONDOM AND METHOD

Inventor: James V. Harmon

U.S. Pat. No. 4,869,723

A condom is provided for enhancing feeling and stimulation on the part of the male by allowing the condom to move, e.g., by a sliding action on the surface of the penis during intercourse. Typically the distal end of the condom is fictionally related to the vagina by weakly bonding the condom to the vagina as by means of a gum-like adhesive agent or by means of a multiplicity of minute fibers bonded on the outside surface of the condom or both. The condom near its open end is held tightly against the base of the penis and, if desired weakly bonded thereto by means of a removable adhesive to form a tight seal.

MALE CONDOM CATHETER HAVING ADHESIVE ON ROLLED PORTION

Inventor: James A. Conway et al.

U.S. Pat. No. Re. 33,206

A male urinal device is disclosed. The device includes a laminated sheath having an inner layer of latex rubber and outer layer of silicone rubber. Adhesive is stored between the inner and outer layers when the sheath is rolled. As the sheath is unrolled, adhesive is released from the outer layer and adheres to the inner layer. Upon pressing the sheath to a penis, a leak-free bond is created.

Each of the above described prior art inventions differ from the present invention and are not anticipated nor obvious with respect to the following items singularly and in combination;
a) condom covering solely the head of the penis,
b) condom having adhesive means contained within the condom functioning to securely fasten said condom to said penis head,
c) angled condom flange functioning to encompass solely said penis head and allow for greater sensation of neuromuscular response during intercourse.
d) additional retaining means contained within the flange portion of said condom functioning as added tightening means around the lip of said penis head.

Numerous condom devices have been provided in prior art. While these units may be suitable for the particular purpose to which they address, they would not be as suitable for the purposes of the present invention as heretofore described.

SUMMARY OF THE INVENTION

It has been discovered, according to the present invention, that for the purpose of holding the condom in its unfolded position during sexual intercourse, it is essential to retain the open end of the condom as close to the body end of the penis of the user as possible. Since condoms are made of very thin rubber type material, it is important to attach the adhesion material to the inside portion of the condom without and insert it over the penis without tearing it. Usually, a condom has a condom rubber band-like ring around its open end which in the present invention snugly fits under the lip on the head of the penis.

It is therefore an object of the present invention to improve a condom and ring securing means of a condom, so the chance of tearing and loosing the condom is greatly reduced.

The novelty of the present invention condom adhesive means is that it is specially designed for retaining a condom which is small, extremely thin and highly flexible. The adhesive means is able to keep the condom in its unrolled position and withstand the natural movement during its usage, yet without tearing up the condom. One unique feature of the present invention condom adhesive means is that its attachment is designed to be tightly affixed to the user's penis, without the flexibility which may allow the condom to easily become loose.

The invention concerns a method for increasing male sensation and heightening enjoyment on the part of the male partner during intercourse while using a condom by allowing or facilitating movement of the penis within the vagina during coitus to increase stimulation of the penis and provide a more natural feel similar to that when no condom is used. Nerve excitation elements can be provided, if desired, within the condom to stimulate the penis as it moves therein during intercourse. A lubricant is preferably provided between the penis and the condom to help it slide against the wall of the vagina which is held in place by the frictional relationship with the vagina. This provides greater stimulation for the male and a much more natural feel than is experienced with an ordinary condom. However, the portion of the condom near the open end will remain in close or tight non-sliding contact with the head of the penis to provide a leak-proof seal. The unique condoms of the present invention can be made to appear almost indistinguishable from conventional condoms. They are easy to apply and use, they are supple, pliable, soft and easily moistened with water or otherwise lubricated just prior to insertion into the vagina. They are non-irritating, have no odor and are safe to use. They will also remain in place during coitus, afterward can be easily removed and have prophylactic characteristics as good as a conventional condom.

In one embodiment, a male condom in accordance with the present invention includes a condom means for fitting about a normal, flaccid penis. The condom means includes a flexibly cylindrical member rolled outwardly upon itself forming consecutively larger rolls. The member has adhesive between and inside of the consecutive rolls. The condom includes means for releasing the adhesive when the condom is unrolled and means for providing an adhesive adhering surface when the member is unrolled. In this fashion, the device may be stored with the adhesive protected between consecutive rolls of the member and used by unrolling the member onto a penis allowing the adhesive to release from the releasing means and adhere to the head penis.

In a preferred embodiment, the male condom is in the form of an external male condom having a sheath or sleeve for fitment about a normal, flaccid penis. The sleeve has an open end and an end opposite which unitarily joins a bulbous surge reservoir. The condom is comprised of an internal layer of latex rubber with an internal layer of an adhesive release agent. In a pre-intercourse position, the sleeve is outwardly rolled upon itself. A pressure sensitive, medical adhesive is located between consecutive rolls. When the sleeve is rolled onto a penis, the adhesive adheres to the latex rubber layer and releases from the release agent layer. In this way, the adhesive is sandwiched between the latex rubber an the penis and upon applying a one time appropriate amount of pressure to the sleeve an penis forms a leak-free bond.

Thus, the method for installing the male condom onto a penis includes the steps of unrolling the condom head onto the penis and pressing the unrolled condom portion against the penis to form completely around the penis a bond between the condom portion and the penis. As indicated the adhesive is released from the outer surface of the condom portion and adheres to the inner surface of the condom portion during the unrolling step.

The device is easily installed on a penis by simply unrolling and pressing. Additional steps of applying an adhesive or applying a tape or a pad have been eliminated.

A primary object of the present invention is to provide a condom that will overcome the shortcomings of the prior art devices.

Another object is to provide a Condom in which only the head of the penis is covered.

An additional object is to provide a Condom in which increased sensitivity is attained during intercourse.

A further object is to provide a Condom that is simple and easy to use.

A still further object is to provide a Condom that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a perspective view of an unrolled condom having a reservoir to collect semen and an internal retaining means within the center of the flange which then becomes integrately secured under the lip on the head of a penis.

FIG. 2 is a cross-sectional view of an unrolled condom having a reservoir to collect semen, adhesive means to securely fasten said condom to the head of said penis, an angled condom opening to solely encompass only the head of the penis, and an internal retaining means within the center of the flange which then becomes integrately secured under the lip on the head of a penis.

FIG. 3 is a cross-sectional perspective view of an unrolled condom encompassing the head of a penis having a reservoir to collect semen, adhesive means to securely fasten said condom to the head of said penis, an angled condom opening to solely encompass only the head of the penis, and an internal retaining means within the center of the flange which then becomes integrately secured under the lip on the head of a penis allowing the rest of the penis to be exposed, thus, increasing sensitivity during intercourse.

DETAILED DESCRIPTION OF THE PREFERRED EMBODIMENTS

Turning now descriptively to the drawings, in which similar reference characters denote similar elements throughout the several views, FIGS. 1 through 3 illustrate a condom 10, which consists of a covering solely the head of the penis, condom having adhesive means contained within the condom functioning to securely fasten said condom to said penis head, an angled condom flange functioning to encompass solely said penis head and allow for greater sensation of neuromuscular response during intercourse, and additional retaining means contained within the flange portion of said condom functioning as added tightening means around the lip of said penis head. The adhesive means is viral tidal, bacteria cidal, or mycocidal. It is hypoallergenic, manufactured from totally organic substances, and is semiadhesive.

Referring now to FIG. 1 which is a perspective view of an unrolled condom 10 having a reservoir 18 to collect semen and an internal retaining means 12 within the center of the flange lip 14 which then becomes integrately secured under the lip 30 on the head of a penis. The reservoir 18 is capable of expansion as more semen enters it during ejaculation. The condom top 16 is longer in length than the condom bottom 20, thus providing and angled condom opening 32 which provides for the maximum amount of penis exposure functioning to allow increased sensation during intercourse.

Referring now to FIG. 2 which is a cross-sectional view of an unrolled condom 10 having a reservoir 18 to collect semen, adhesive means 22 to securely fasten said condom 10 to the head 28 of said penis, an angled condom opening 32 to solely encompass only the head 28 of the penis, and an internal retaining means 12 within the center of the flange lip 14 which then becomes integrarely secured under the lip 30 on the head 28 of a penis. The adhesive means 22 is positioned throughout the top 16 and bottom 20 portion of the condom 10 to securely fasten said condom 10 to the head 28 of a penis. The adhesive means excludes the furthest most tip of the penis where the reservoir 18 is located at the corresponding place on the condom 10 in order to allow the maximum expansion of reservoir space during ejaculation.

Lastly, referring to FIG. 3 which is a cross-sectional perspective view of an unrolled condom 10 encompassing the head 28 of a penis having a reservoir 18 to collect semen, adhesive means 22 to securely fasten said condom to the head 28 of said penis, an angled 32 condom opening 32 to solely encompass only the head 28 of the penis, and an internal retaining 12 means within the center of the flange lip 14 which then becomes integrately secured under the lip 30 on the head of a penis allowing the rest of the penis shaft 24 to be exposed, thus, increasing sensitivity during intercourse. The retaining means 12 is anglurly designed in a functional relationship to encompass the angle of the lip 30 of the head of the penis and the angle of the penis shaft 24, thus, forming a more secure fastening arrangement between penis and condom. The adhesive means 22 is positioned throughout the top 16 and bottom 20 portion of the condom 10 to securely fasten said condom 10 to the head 28 of a penis. The adhesive means excludes the furthest most tip of the penis where the reservoir 18 is located at the corresponding place on the condom 10 in order to allow the maximum expansion of reservoir space during ejaculation of sperm from the opening at the head of the penis 26. The retaining means 12 is designed as a first angle that parallels an angle of the penis head 30 and a second angle that parallels an angle of the penis shaft 24.

LIST OF REFERENCE NUMERALS

10—CONDOM
12—RETAINING MEANS
14—FLANGE LIP

16—CONDOM TOP
18—RESERVOIR
20—CONDOM BOTTOM
22—ADHESIVE MEANS
24—PENIS SHAFT
26—PENIS OPENING
28—PENIS HEAD
30—PENIS HEAD LIP
32—ANGLED CONDOM OPENING

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letter Patent is set forth in the appended claims:

1. An improved condom comprising;
   a) a fluid and microorganism proof cover solely encompassing a head of a penis, having adhesive means contained within the inside functioning to securely fasten said condom to said penis head,
   b) an angled condom flange functioning to encompass solely said penis head, thus, allowing maximum exposure of the remainder of a penis shaft allowing for increased sensation of neuromuscular response during intercourse,
   c) an additional mechanical retaining means contained within the center of said flange portion of said condom functioning as an added tightening means around the lip of said penis head, and
   d) a reservoir located at the terminus end of said condom functioning to collect said fluid and microorganisms during ejaculation.

2. A condom as described in claim 1, whereas said adhesive means is not present at a tip of said condom to allow maximum expansion of said reservoir, thus collecting maximum amounts of ejaculate.

3. A condom as described in claim 2, whereas said adhesive means is viral cidal.

4. A condom as described in claim 2, whereas said adhesive means is bacteria cidal.

5. A condom as described in claim 2, whereas said adhesive means is mycocidal.

6. A condom as described in claim 2, whereas said adhesive means is hypoallergenic.

7. A condom as described in claim 2, whereas said adhesive means is manufactured from totally organic substances.

8. A condom as described in claim 2, whereas said adhesive means is semi-adhesive, thus, allowing easy removal of said condom from said penis.

9. A condom as described in claim 1, whereas said adhesive means is coated entirely throughout an inside layer of said condom except said tip of said condom reservoir.

10. A condom as described in claim 2, whereas said adhesive means is spermicidal.

11. A condom as described in claim 1, whereas said retaining means is designed with a first angle paralleling an angle of a lip of a penis and a second angle parallelling a shaft of a penis functioning to more securely affix said condom around, over said lip of said penis.

12. A condom as described in claim 1, whereas said condom is manufactured from a group of pliable and expandable materials singuraly and in combination such as rubber, latex, skin, epidermal tissue, endodermal tissue, smooth muscle tissue, plastic and plastic composites.

13. A condom as described in claim 1, whereas said condom having a shortened bottom portion and a longer top portion corresponding to the length of the underside and top of a penis head, thus, said condom is angled at its open terminus end when unrolled.

14. A condom as described in claim 1, whereas said retaining means is integrately molded within said flange portion of said condom.

15. A condom as described in claim 1, whereas said reservoir is half an hour-glass in shape functioning to maximally contain ejaculate.

16. A condom as described in claim 1, whereas said condom is double walled functioning to prevent breakage.

17. A condom as described in claim 1, whereas said reservoir is thickened in manufacture as compared to the rest of said condom structure functioning to allow expansion of said reservoir without breakage.

* * * * *